United States Patent [19]

Terada et al.

[11] Patent Number: 4,560,511

[45] Date of Patent: Dec. 24, 1985

[54] METHOD OF PRODUCING SHIKONIN

[75] Inventors: Akira Terada, Munakata; Yasuhiro Tanoue, Kitakyushu, both of Japan

[73] Assignee: Kyushu Institute of Technology, Kitakyushu, Japan

[21] Appl. No.: 593,135

[22] Filed: Mar. 26, 1984

[30] Foreign Application Priority Data

Mar. 26, 1983 [JP] Japan ................................ 58-50801

[51] Int. Cl.$^4$ ...................... C07C 50/14; C07C 50/12
[52] U.S. Cl. ............................ 260/396 R; 260/396 K
[58] Field of Search ....................... 260/396 R, 396 K

[56] References Cited

U.S. PATENT DOCUMENTS 4,282,250 8/1981 Papageorgiou ................. 260/396 R

FOREIGN PATENT DOCUMENTS 1925299 11/1969 Fed. Rep. of Germany ... 260/396 R

OTHER PUBLICATIONS

*Tetrahedron Letters*, No. 19(1959) pp. 9–13, Farina, "A New Method for the Preparation of Naphtozorims."
Patai, *The Chemistry of the Quinonoid Compounds*, part 1, 1974, p. 134.
Y. N. Shukla et al., Experientia 25, 357 (1969).
U. Sankawa et al., Chem. Pharm. Bull. (Tokyo) 25, (9), 2392–2395 (1977).
U. Sankawa et al., Chem. Pharm. Bull. (Tokyo) 29, (1) 116–122, (1981).
M. Tabata et al., Abstract of Papers, 100th Annual Meeting of Pharm. Society of Japan (1980) p. 249.

*Primary Examiner*—Glennon H. Hollrah
*Assistant Examiner*—Raymond Covington
*Attorney, Agent, or Firm*—Fleit, Jacobson, Cohn & Price

[57] ABSTRACT

A method of producing shikonin, having the following chemical structure

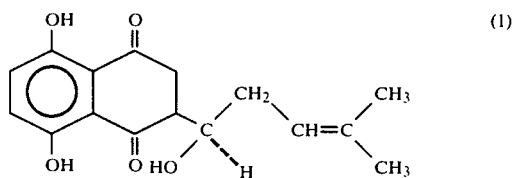

which method comprises dehydrating 2-(1'-acetoxy-4'-hydroxy-4'-methylpentyl)-5,8-diacetoxy-1,4-naphthoquinone, treating the resulting product with an alkali hydroxide and acidifying the treated product.

2 Claims, 1 Drawing Figure

METHOD OF PRODUCING SHIKONIN

BACKGROUND OF THE INVENTION (1) Field of the Invention:

This invention relates to a method of producing shikonin.

(2) Description of the Prior Art:

Purple shikonin is a foundamental member of the purple pigments, which is extracted from violet root (*Lithospermum erythrorhizon*, Japanese name "Shikon") since the old ancient times in the orient. It is not only famous as a "Shikonzome" (shikon-dyed cloth) as included in the treasure of the Shosoin, a Japanese ancient temple, but also is applauded as an ointment for tumor, scald, hemorrhoids and the like owing to its antipyretic and alexipharmic actions. Shikonin is originally known as a famous Chinese medicine as described in a botany of Honzokomoku from old times.

It has been found that shikonin is effective as an antibacterial substance. Recently, shikonin has also been found to be effective as an anticancer agent.

Shikonin is very low in toxicity and is easily used in the coloration of wines. However, due to its scarcity in Japan, it has to be imported. It is regretable that this compound has not been successfully synthesized up to now.

SUMMARY OF THE INVENTION

It is, therefore, an object of the invention to provide a method of cheaply producing shikonin in industry and in mass production.

According to the invention, shikonin is produced by dehydrating 2-(1'-acetoxy-4'-hydroxy-4'-methylpentyl)-5,8-diacetoxy-1,4-naphthoquinone, treating the resulting product with an alkali hydroxide, and acidifying the thus treated product.

DETAILED DESCRIPTION OF THE INVENTION

Figure 1:
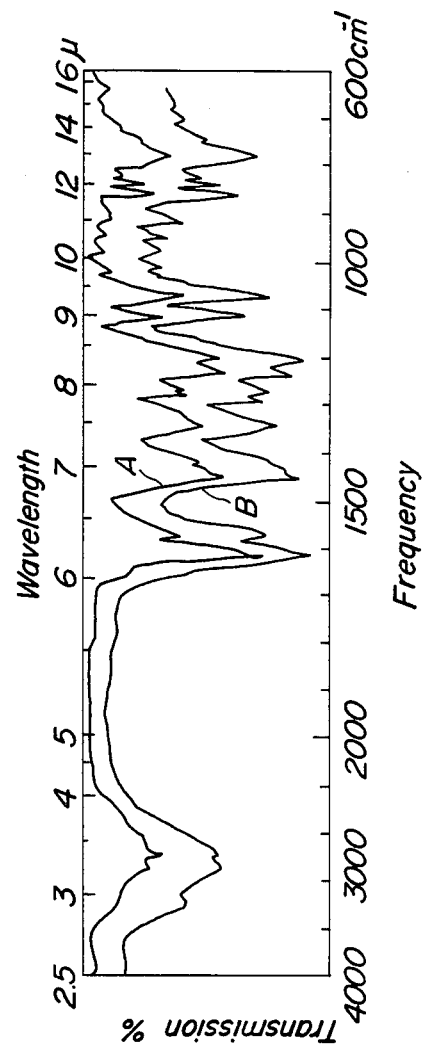
FIG. 1 is an infrared absorbtion spectrum of a synthesized shikonin racemic compound and natural shikonin.

Shikonin has a chemical structure of absolute configuration represented by the following formula (1):

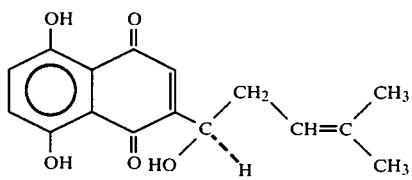

(1)

In the formula (1), a compound having an OH group oppositely positioned at α-position of the side chain alkenyl group (behind paper) is alkannin as an optical antipode of shikonin. Alkannin is a reddish brown coloring matter extracted from roots of *Alkanna tinctoria* is Europe and is also used in purple-dying.

It has been reported that a soft shikon recently imported from China as a starting material of shikonin was alkannin type as an optical antipode of shikonin.

The invention is directed to a method for chemically synthesizing shikonin. The method produces a mixture of shikonin (+) and alkannin (−) with a ratio (%) of 50:50, that is, as a racemic compound.

2-(1'-Acetoxy-4'-hydroxy-4'-methylpentyl)-5,8-diacetoxy-1,4-naphthoquinone is easily synthesized by starting from 2-formyl-1,4,5,8-tetramethoxynaphthalene, which was previously produced as a novel compound by the inventors, through four steps.

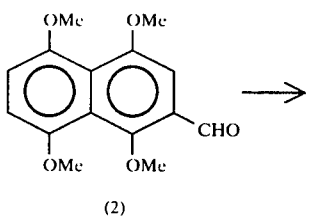

(2)

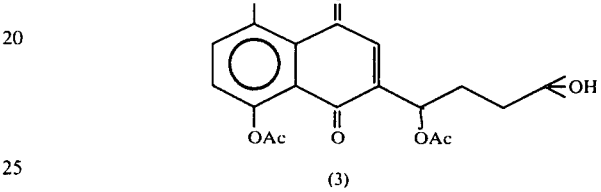

(3)

According to the invention, the compound of the formula (3) is reacted with a dehydrating agent such as phosphorus pentoxide, thionyl chloride or the like to obtain a mixture of 2-(1'-acetoxy-4'-methyl-3'-pentenyl)-5,8-diacetoxy-1,4-naphthoquinone [structural formula (4)] and 2-(1'-acetoxy-4'-methyl-4'-pentenyl)-5,8-diacetoxy-1,4-naphthoquinone [structural formula (5)]. In this case, the yield of the compound of the formula (4) is advantageously 3 times or more than that of the compound of the formula (5).

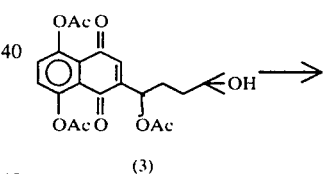

(3)

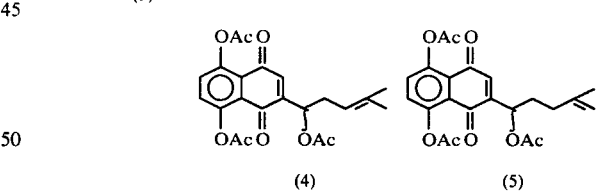

(4)      (5)

After the dehydration step, the compound defined by formula (4) is separated from the compound of the formula (5), dissolved into an alkali hydroxide and then acidified to easily precipitate reddish brown needle crystals of shikonin racemic body represented by the structural formula (6).

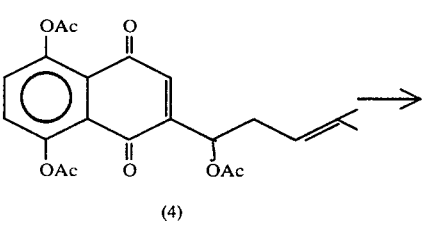

(4)

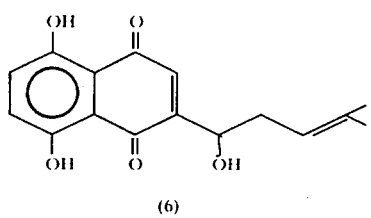

(6)

The following examples are given in illustration of the invention, but are not intended as limitations thereof.

EXAMPLE 1

2-(1'-acetoxy-4'-methyl-3'-pentenyl)-5,8-diacetoxy-1,4-naphthoquinone [formula (4)]

Two hundred and thirty one parts of 2-(1'-acetoxy-4'-hydroxy-4'-methyl-pentyl)-5,8-diacetoxy-1,4-naphthoquinone [formula (3)] were dissolved into 1,500 parts of pyridine, which was cooled down to −38° C. and gradually added dropwise with 70 parts of thionyl chloride. The resulting solution was stirred for seven minutes and then poured into ice water. The cooled solution is then extracted with methylene chloride, with the extract being washed with an aqueous solution of sodium bicarbonate and further with brine, dried over anhydrous sodium sulfate, and then concentrated to produce 168 parts of a crude product. This product was separated by a silica gel chromatography to give 93 parts of compound of the formulae (4) and (5) at a ratio of 3:1 in a yield of 46%. The identification was made through the fact that the compound of the formula (4) has an absorption assigned to a hydrogen of a trisubstituted olefin at 5.07 ppm by nuclear magnetic resonance (NMR) analysis, while the compound of the formula (5) has an absorption assigned to a hydrogen of a vinylidene group at 4.69 ppm by NMR analysis and an adsorption of 890 cm$^{-1}$ assigned to vinylidene by infrared spectroscopic analysis.

EXAMPLE 2

Thirty two parts of the compound of the formula (3) was dissolved into 1,500 parts of methylene chloride and then cooled in an ice bath. To this mixture 30 parts of phosphorus pentoxide was added to the solution and vigorously stirred for 10 minutes. After stirring for 10 minutes the solution was poured into ice water and then extracted with methylene chloride. The resulting extract was subjected to the same work-up as described in Example 1 to obtain 22 parts of a crude product. This product was separated into compounds of the formulae (4) and (5) at a ratio of 10:1.

EXAMPLE 3

2-(1'-hydroxy-4'-methyl-3'-pentenyl)-5,8-dioxy-1,4-naphthoquinone [shikonin racemic body of the formula (6)]

To 63 parts of the compound of the formula (4) obtained in Example 1 or 2 was added 5,000 parts of N-sodium hydroxide and the resulting solution was stirred in a water bath for 3 hours. After filtration, the resulting filtrate was gradually added with glacial acetic acid, while being cooled in an ice bath, until the color of the filtrate changed from dark blue (purple) to red. After the extraction with methylene chloride, the resulting extract was subjected to the similar work-up and then condensed to obtain 25 parts of a crude product of the formula (6). The crude product was dissolved into chloroform, which was separated by a chromatography of a silica gel column to obtain 16 parts of reddish brown pure crystals of the shikonin racemic compound of the formula (6). The resulting racemic compound had a melting point of 146°–148° C. (authentic value: 148° C.) and elementary analytical values of C: 66.34% and H: 5.60% (calculated values as $C_{16}H_{16}O_5$, C: 66.66%, H: 5.59%). All analytical data of the racemic body by NMR, ultraviolet and visible spectroscopics, mass spectrum and the like are well in conformity with those of natural shikonin. By way of an example, the result of the infrared spectroscopic analysis is shown in FIG. 1, wherein a line A is a result of the synthesized shikonin racemic compound, and a line B is a result of natural shikonin. It can be seen from FIG. 1, that the spectra of both the products are well in conformity with each other.

What is claimed is:

1. A method of producing shikonin, which comprises dehydrating 2-(1'-acetoxy-4'-hydroxy-4'-methylpentyl)-5,8-diacetoxy-1,4-naphthoquinone, with phosphorous pentoxide or thionylchloride treating the resulting product with an alkali hydroxide, and then acidifying the thus treated product.

2. The method of claim 1 wherein the alkali hydroxide is sodium hydroxide.

* * * * *